(12) United States Patent
Baker et al.

(10) Patent No.: US 10,977,823 B2
(45) Date of Patent: Apr. 13, 2021

(54) OBJECT RECOGNITION AND DATA RETRIEVAL SYSTEM

(71) Applicant: RST Automation LLC, Bronx, NY (US)

(72) Inventors: Russell Baker, Sunnyside, NY (US); Lawrence Zelner, New York, NY (US)

(73) Assignee: RST AUTOMATION LLC, Bronx, NY (US)

(*) Notice: Subject to any disclaimer, the term of this patent is extended or adjusted under 35 U.S.C. 154(b) by 0 days.

(21) Appl. No.: 16/397,178

(22) Filed: Apr. 29, 2019

(65) Prior Publication Data

US 2019/0333244 A1    Oct. 31, 2019

Related U.S. Application Data (60) Provisional application No. 62/664,328, filed on Apr. 30, 2018.

(51) Int. Cl.
*G06K 9/00* (2006.01)
*G06T 7/73* (2017.01)

(52) U.S. Cl.
CPC .................................. *G06T 7/74* (2017.01)

(58) Field of Classification Search
CPC combination set(s) only.
See application file for complete search history.

(56) References Cited

U.S. PATENT DOCUMENTS

2013/0336554 A1* 12/2013 Lewis ............... G06K 9/00
                                                                   382/128
2015/0324739 A1    11/2015 Baker et al.
2016/0264275 A1    9/2016  Baker et al.

* cited by examiner

*Primary Examiner* — Alex Kok S Liew
(74) *Attorney, Agent, or Firm* — Arent Fox LLP (57) ABSTRACT

An object recognition and data retrieval system interfaces with a target system, such as an automated storage cabinet, to share object data for storage and retrieval.

13 Claims, 9 Drawing Sheets

OBJECT RECOGNITION AND DATA RETRIEVAL SYSTEM

CROSS REFERENCE TO RELATED APPLICATIONS

This application claims priority under 35 U.S.C. § 119(e) of U.S. Provisional Application No. 62/664,328, filed on Apr. 30, 2018, entitled "Object Recognition and Data Retrieval System," the disclosure of which is hereby incorporated by reference.

STATEMENT REGARDING FEDERALLY SPONSORED RESEARCH OR DEVELOPMENT

N/A

BACKGROUND

Many businesses have a need to store a large number of objects. For example, companies in the medical industry, such as hospitals, must store a large number of medical instruments. Generally, to look up the data for an object, the name or an identification number of the object must be entered manually and/or through a search function.

For example, a sterile supply department in a hospital must provide storage and inventory of surgical instruments. These data are often stored within the instrument tracking system in the department. In order to find the storage and inventory data, the instrument must be looked up in the tracking system software.

Some users employ barcodes on objects. For those users it may be possible to scan the object to retrieve the storage location and other data related to that object type. Barcodes are costly to apply and deteriorate. For example, the process for cleaning and sterilizing surgical instruments is known to degrade barcodes. As such they are typically reserved for specialty instruments.

SUMMARY

An object recognition and data retrieval system is provided that uses a digital representation of a physical object to retrieve data related to that object. The device compares stored digital representations of physical objects to an object under examination to determine the type of object. Once the type is identified, data related to the object is retrieved. The object recognition and data retrieval system can be configured to create and manipulate specific pieces of the data retrieved. The object recognition and data retrieval system can be configured to share object data with other, target storage systems. The shared object data can be used by the target storage system to store the objects.

DESCRIPTION OF THE DRAWINGS

Reference is made to the following detailed description taken in conjunction with the accompanying drawings in which.

DETAILED DESCRIPTION

An object recognition and data retrieval system (ORDRS) is provided that recognizes an object and facilitates viewing, creating, editing and employing data related to that object.

Figure 1:
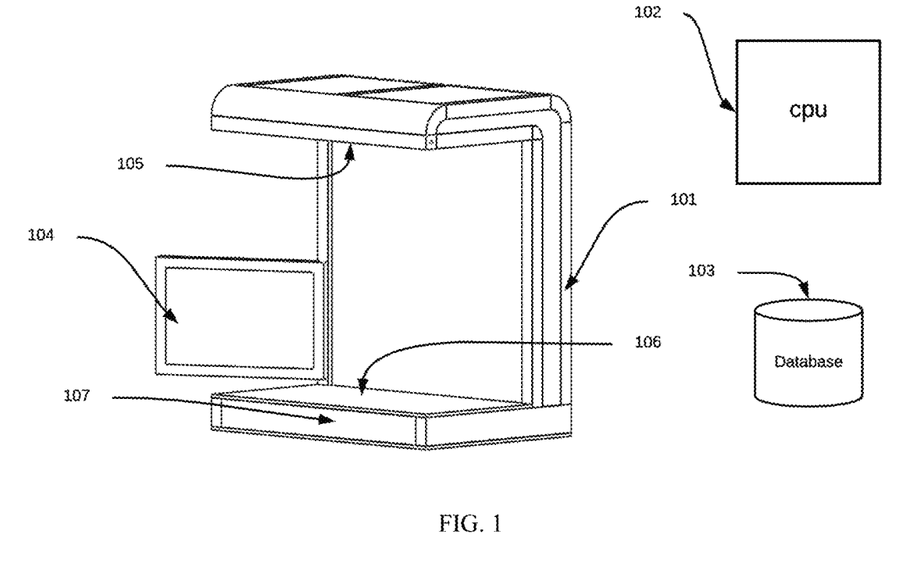
FIG. 1 is a schematic illustration of an embodiment of an object recognition and data retrieval system.
Figure 1A:
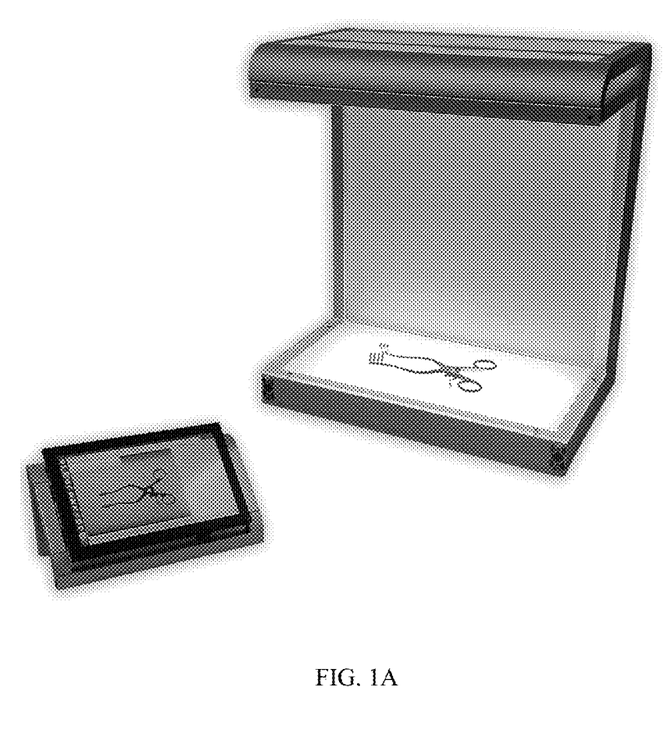
FIG. 1A is an illustration of an object recognition data acquisition device of FIG. 1 supporting an object and a touch screen monitor depicting an image of the object.

Referring to FIGS. 1 and 1A, some embodiments of the system include a body 101 that provides structure for the system as well as attachment points for the various other components. A computer 102 can be used to operate system software. A database 103 can be stored internally on the system computer's hard drive or located on a central or cloud server. The system can include input and/or output devices, such as a touch screen 104, for displaying relevant information to users of the system and to accept input from the user. Buttons on the touchscreen can be used to navigate the software, although external buttons, voice control, or any other suitable manner may be used for system control. An object recognition data acquisition device 105 can be used to record data used for determining the type of object. In some embodiments, the object recognition data acquisition device can include a camera; in some embodiments, the object recognition data acquisition device can be a linear scanner, a range finder, one or multiple cameras, or any other element suitable for acquiring a digital representation of physical objects. A platform 106 can be present on the system as a designated location for placing an object that the user wishes to recognize. Lighting 107 can be employed to improve the reliability of the data acquisition device 105. In some embodiments of the system, backlighting can be employed, for example, through use of a translucent platform 106, for example, a frosted glass or acrylic plate, having a light plate or lighting disposed underneath. Other lighting techniques can be employed. Software on the computer can be used to operate the various components. FIG. 1A illustrates a data acquisition device 105 with a medical or surgical instrument to be recognized and a touch screen monitor displaying an image of the instrument.

Figure 2:
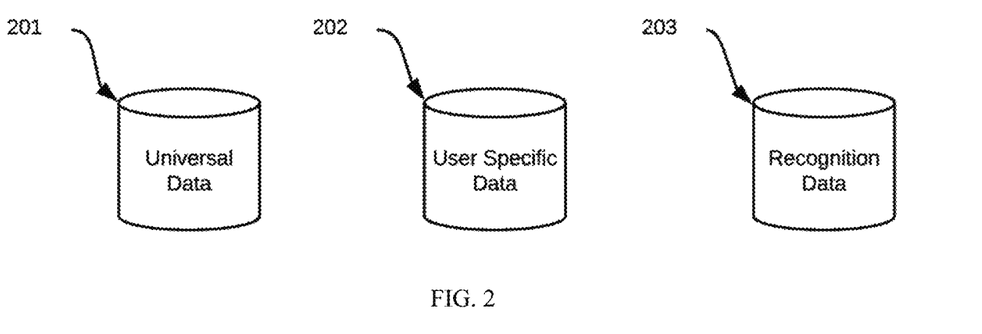
FIG. 2 is a schematic illustration of a database for use with embodiments of an object recognition and data retrieval system.

FIG. 2 shows a representation of a database and data stored within it. Universal data 201 can include general data related to the objects. The universal data can include, but is not limited to, a standardized name, manufacturer(s) of the object, manufacturer(s) respective identification numbers, and categorizations of the object. User specific data 202 can include data that relates to a specific object that applies to a particular user. This can include, but is not limited to, a colloquial name used by a particular user, a preferred manufacturer, and a storage location. Recognition data 203 can include all data relevant to recognizing the objects. This can include, but is not limited, to images, measurements, and barcode and RFID values if used.

Figure 3:
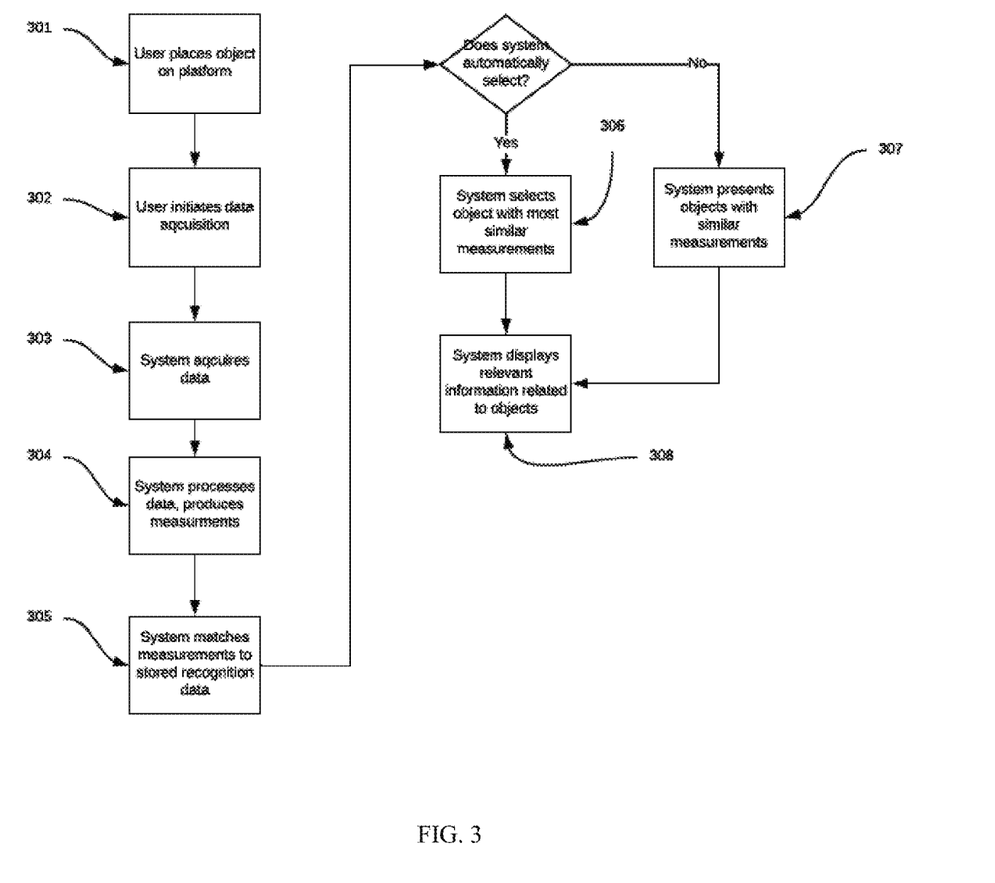
FIG. 3 is a flow chart of an object recognition process.

Embodiments of a recognition process are described with reference to the flow chart in FIG. 3. The data acquisition device can be, for example, a digital camera connected to the computer, for example, using a USB connection. The recognition process begins with the user placing the object on the platform, at step 301. The user then instructs the system to acquire the recognition data for the currently placed object, at step 302. The system acquires the data at step 303 and then processes the data at step 304. The processing of the data results in measurements related to the placed object. These measurements are compared with measurements stored in the database to find the object or objects with the most similar measurements at step 305. In some embodiments, the object type with stored measurements nearest to the processed measurements is automatically selected at step 306. In some other embodiments, the object types with stored measurements nearest to the processed measurements are presented to the user for selection at step 307. In both cases, relevant data related to the object type or types can be displayed for the user at step 308.

The object recognition and data retrieval system can be implemented to accomplish a variety of tasks. In some embodiments, the system can serve as a storage locator and inventory control manager. In some embodiments, the system can implement several functions with regard to storage locating and inventory control, including but not limited to viewing and editing the current inventory records, placing objects into storage and updating the inventory records, retrieving objects from storage and updating the inventory records, as well as any other functions relevant to storage, retrieval and inventory management.

Figure 4:
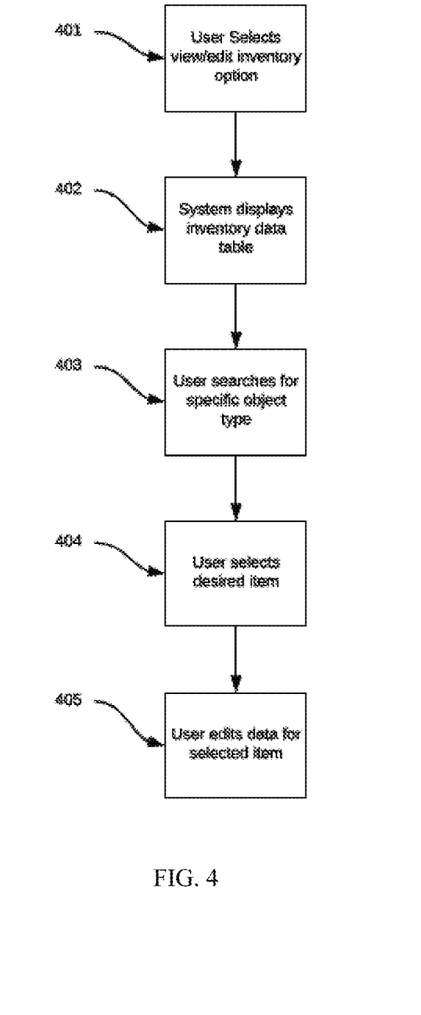
FIG. 4 is a flow chart of an inventory editing process.

An exemplary process flow for viewing and editing inventory information for the storage system is shown in FIG. 4. To begin, the user selects the "View/Edit Inventory" function from a function selection screen at step 401. The system displays a table of objects along with relevant data such as stored quantity and storage location at step 402. The system additionally displays a search field for limiting the number of presented items. The user enters text into the field to find the item they are searching for at step 403. Upon finding the desired item, the user selects the item at step 404. The user may then choose to edit information related to the item at step 405.

Figure 5:
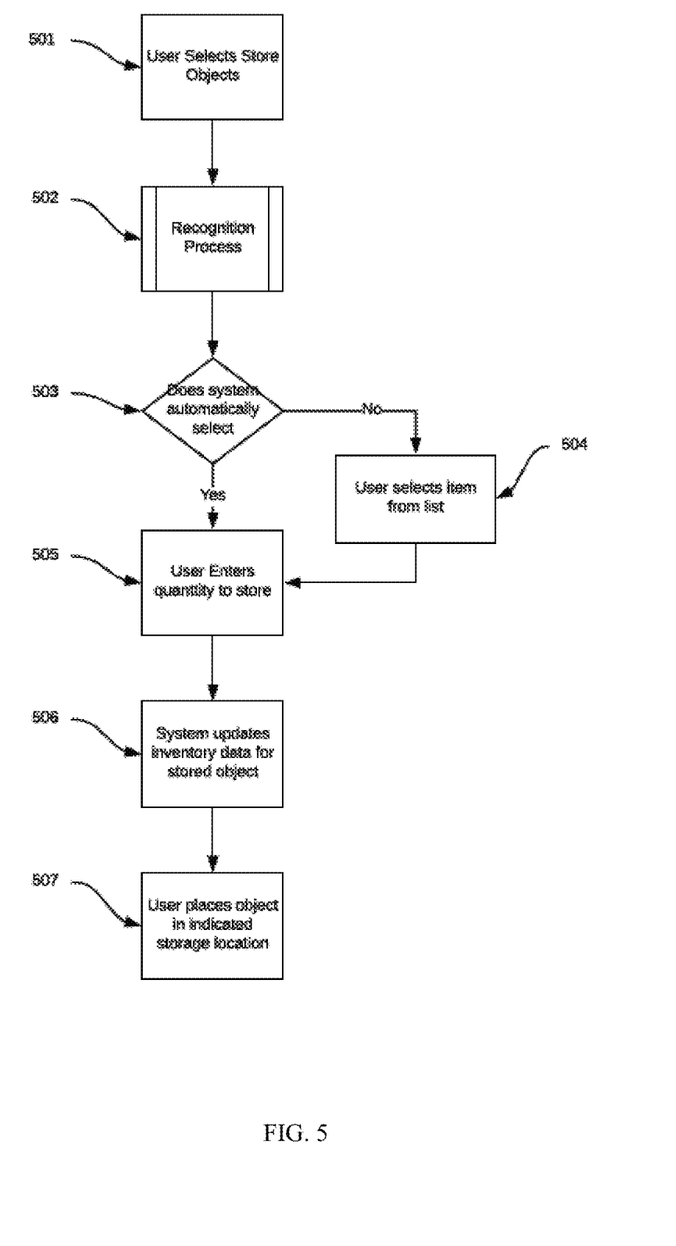
FIG. 5 is a flow chart of a process for storing an object.

An exemplary process flow for adding objects to storage and updating inventory records is shown in FIG. 5. To begin, the user selects the "Store Objects" function from a function selection screen at step 501. This process can begin with the recognition process as shown for example in FIG. 3, at step 502. Related to step 308 in FIG. 3, the system software can display the storage location and other relevant information for presented items. Next there is a decision in the process flow depending on whether or not the system automatically selects the object type at step 503. If it does not, the user may select the object type at step 504. Following user selection or automatic selection by the system, the user enters a quantity for a number of instances of the object being added to inventory at step 505. Upon entering the quantity, the system software updates the database to reflect the change in inventory quantity for the selected object at step 506. The user then places the object into the storage location indicated by the system software at step 507.

Figure 6:
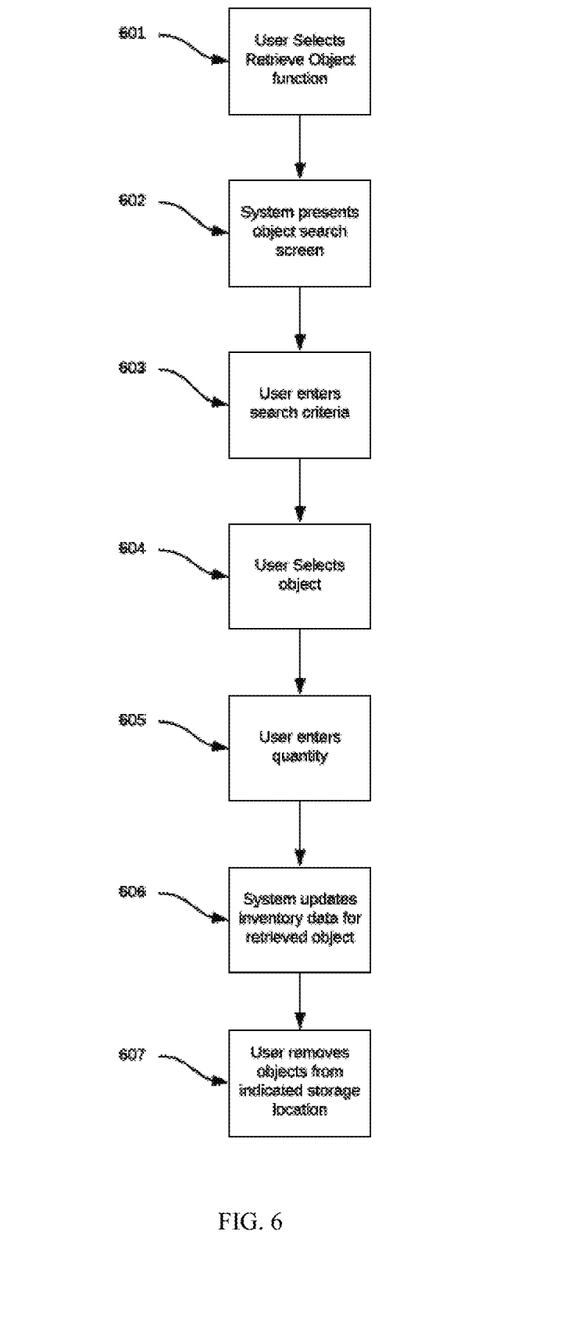
FIG. 6 is a flow chart of a process for retrieving an object.

An exemplary process flow for retrieving objects from storage for an embodiment of the storage system is shown in FIG. 6. To begin, the user selects the "Retrieve Object" function from a function select screen at step 601. The system presents an object search screen to the user at step 602. The system may provide a variety of ways to limit the returned search values. These may include matching text of the name, catalog number or other relevant text for the object, selection of a category of object, size descriptions, or any other relevant data which may help to shorten the length of returned objects list. Following the flow chart, the user can enter search criteria at step 603. As the potential objects are displayed, they include data related to storage and inventory, including, but not limited to, storage location and current inventory quantities. Upon finding the desired object, the user selects the object at step 604. The user then enters the quantity of the object they would like to remove at step 605. The system then updates the inventory data for the object at step 606. Last, the user retrieves the objects from the storage location displayed by the system at step 607.

Figure 7:
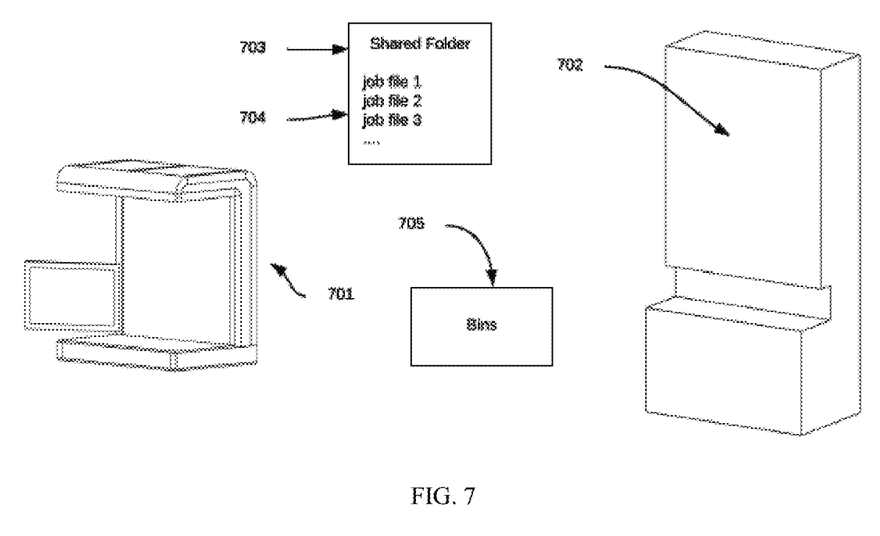
FIG. 7 is a schematic illustration of an embodiment of an object recognition and data retrieval system interfacing with a target system comprising an automated storage cabinet.

The object recognition and data retrieval system (ORDRS) may be implemented to interface and provide executable data to external target systems. In some embodiments, the system can interface with a system of automated storage cabinets (ASC). An exemplary configuration of the system interfaced with the ASC is shown in FIG. 7. The configuration includes an ORDRS 701, an ASC 702, a shared folder 703, job files within the shared folder 704, and staging bins 705. The shared folder is a folder that can be accessed by the ASC, and to which the ORDRS may write files. The folder may be located on the hard drive of the computer system of the ORDRS, of the ASC, or on an external computer. The folder may be a shared network folder, or accessible using FTP with the system as the client, or using any other manner of placing a file into a folder. The job files in the folder can contain tables of information representing a list of objects to store. Job files can be formatted such that the ASC may extract executable data from the file. The ASC can regularly scan the shared folder for job files. The ASC can display found job files on a monitor. A user can then select a job file and execute the job with the ASC. Objects can be placed in the staging bins after being added to the job file.

In some embodiments, a job file can be built as objects are recognized. In some embodiments, each line of a job file can include an object identification and a location, such as a bin number, to which the object is to be transferred for storage, and a quantity of the objects to be stored at that location.

Figure 8:
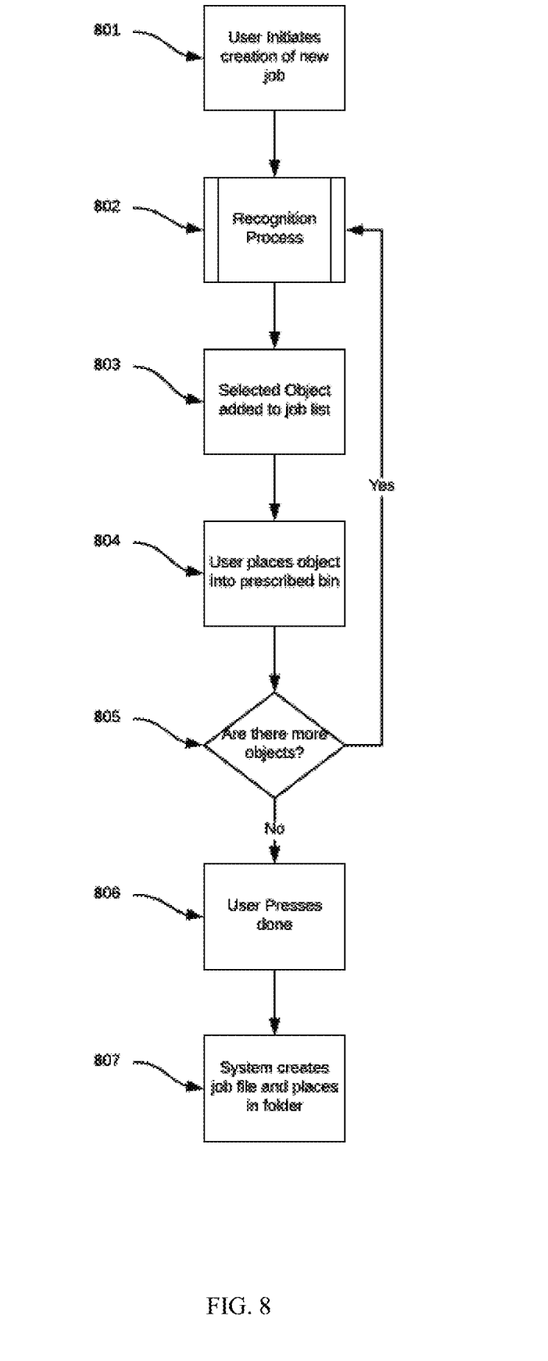
FIG. 8 is a flow chart of a process for creating a job list of objects to be stored.

Some embodiments of the system can be implemented to interface with the ASC, the system can be configured to create jobs for adding objects to the ASC inventory. FIG. 8 displays an exemplary flow chart of a job file creation and submission process. First, a user initiates the creation of a new job at step 801. To populate the job with objects to be stored, in some embodiments, the recognition process of FIG. 3 can be followed at step 802. After an object type is selected, the object is added to the job list at step 803. In some embodiments the job list can be displayed on the monitor. Next, the user is instructed to place the object into a numbered staging bin at step 804. In some embodiments, the system increases the staging bin number for each successive object type such that the staging bin number for the object equals the line number in the jobs list. Steps 802 through 804 can be repeated until there are no more objects or until a maximum number of staging bins is occupied, at step 805. When the job is complete, the user presses done at step 806, and the system creates the job file and places it in the shared folder at step 807.

In operation, the ASC can position the shelving to a loading or unloading position such that the object to be retrieved or stored is accessible. Because the ASC can be quite large, when executing a job the ASC may be configured to execute the job in the order requiring the least amount of motion. This may not be the order of the objects in the job file.

Figure 9:
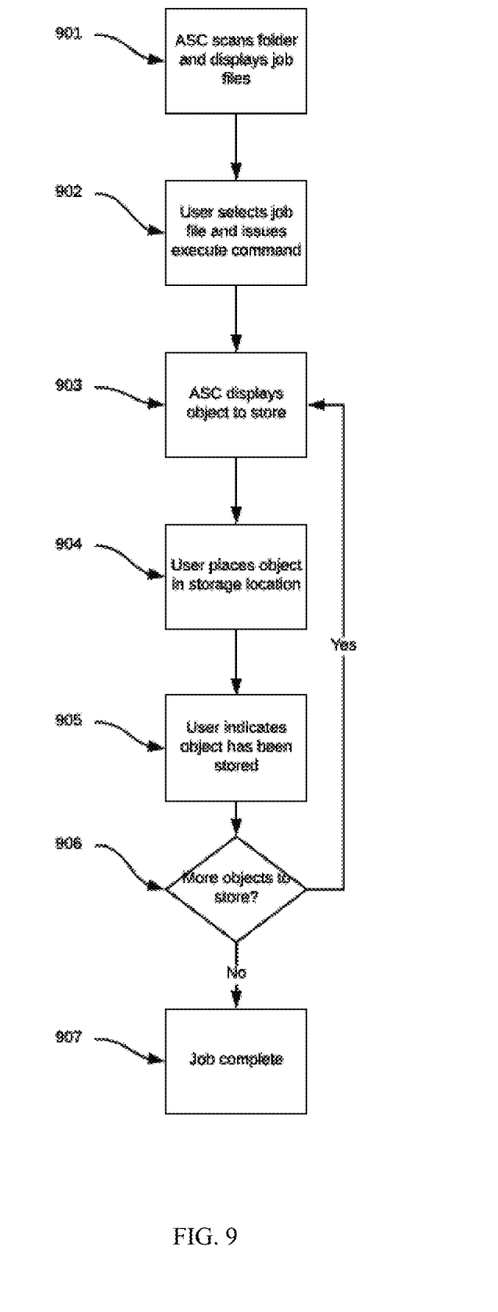
FIG. 9 is a flow chart of a process for executing a job by an automated storage cabinet.

The flow chart in FIG. 9 shows an exemplary process for executing a job file created by the system on the ASC. First, the ASC scans the folder and displays the job files at step 901. The user then selects the desired job file and commands the ASC to execute the job at step 902. The ASC informs the user of the object to be stored at step 903. In some embodiments, the ASC can display the name and the job line number that correspond to the staging bin number. Once the ASC reaches position, the user may place the object in the storage location, at step 904. Then the user indicates they have stored the object at step 905. Steps 903 through 905 can be repeated until there are no more objects to store, at step 906, and the job is complete at step 907.

Figure 10:
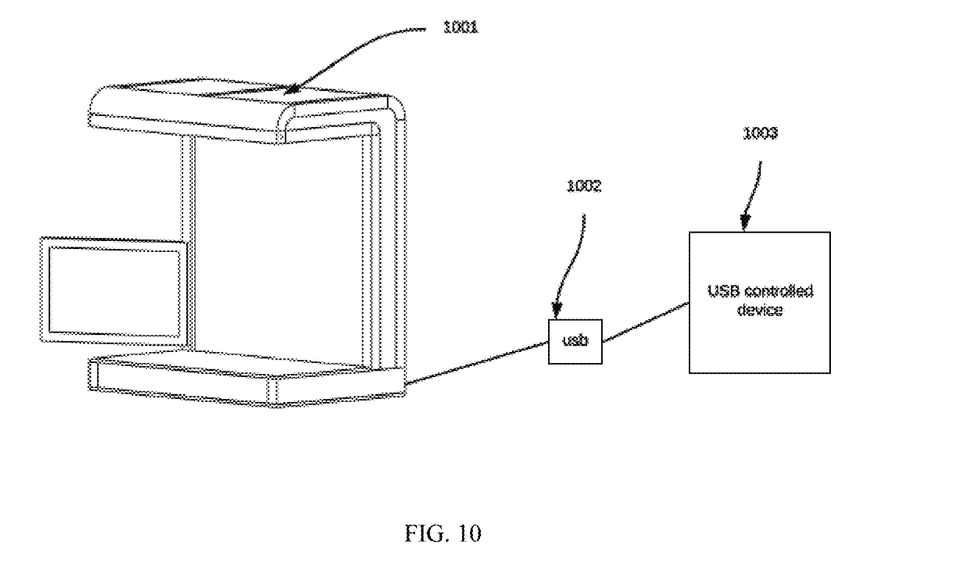
FIG. 10 is a schematic illustration of a further embodiment of an object recognition and data retrieval system for use with a bar code identification system.

In some embodiments, the object recognition and data retrieval system can be configured to provide a barcode reader functionality to a target external system. For example, some storage systems may employ a barcode input to track stored objects. Referring to FIG. 10, some embodiments can include an object recognition and data retrieval system (ORDRS) 1001, a barcode output 1002, and a system that employs a barcode input 1003. Barcode output is typically a string of characters followed by a carriage return and may be transmitted via, for example, USB cable or any other suitable manner.

Figure 11:
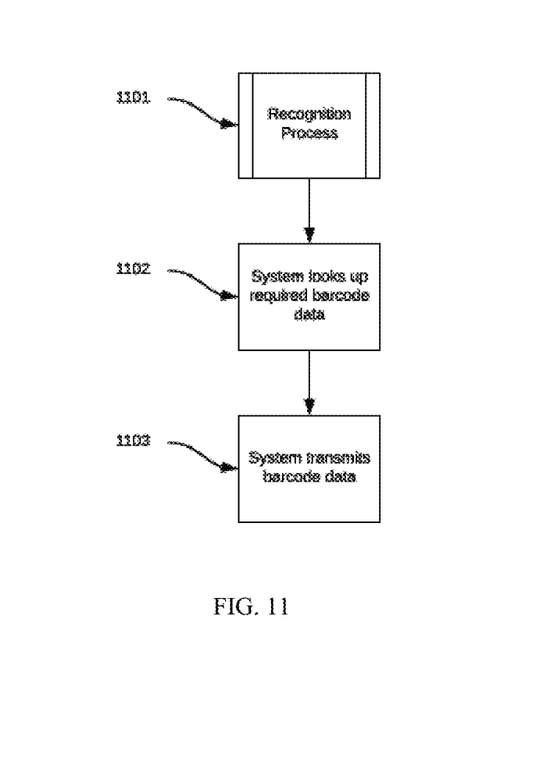
FIG. 11 is a flow chart of a process for transmitting a bar code identification to a target system.

FIG. 11 shows a flow chart of an ORDRS employing a barcode output to control a target system. The process can begin, at step 1101, with a recognition process such as described above with reference to FIG. 3. The ORDRS can look up the required data to be transmitted as barcode output at step 1102. Next, the barcode output is transmitted to the target system at step 1103. For example, an ASC, such as described above, may be configured to accept barcode input. In such a configuration, an object identifier shared between the ORDRS and the ASC representing one specific object type can be sent in the barcode output. Upon receipt, the ASC can navigate to the storage location for the specified identifier.

In some embodiments, the system can interface with objects identified using a radio frequency identification tag (RFID).

As described above, a user initiates each instance of recognition. It will be appreciated that in some embodiments, the object recognition process can be continuous.

In some embodiments, a user may also search for a type of object, which may be necessary if an object is too large to fit into a field of view of a camera of an object recognition device.

In some embodiments, the system can be configured to send single item jobs. In this case, a user does not start or end a job. Each time an object is processed, the system creates and sends a job. Numbered bins would not be used or needed.

The computer system that executes programming for the object recognition and data retrieval system as described herein can be implemented as or can include a computing device that includes a combination of hardware, software, and firmware that allows the computing device to run an applications layer or otherwise perform various processing tasks. Computing devices can include without limitation personal computers, work stations, servers, laptop computers, tablet computers, mobile devices, hand-held devices, wireless devices, smartphones, wearable devices, embedded devices, microprocessor-based devices, microcontroller-based devices, programmable consumer electronics, minicomputers, main frame computers, and the like.

The computing device can include a basic input/output system (BIOS) and an operating system as software to manage hardware components, coordinate the interface between hardware and software, and manage basic operations such as start up. The computing device can include one or more processors and memory that cooperate with the operating system to provide basic functionality for the computing device. The operating system provides support functionality for the applications layer and other processing tasks. The computing device can include a system bus or other bus (such as memory bus, local bus, peripheral bus, and the like) for providing communication between the various hardware, software, and firmware components and with any external devices. Any type of architecture or infrastructure that allows the components to communicate and interact with each other can be used.

Processing tasks can be carried out by one or more processors. Various types of processing technology can be used, including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, scripts, drivers, objects, components, data structures, and the like that perform particular tasks or operate on data.

Processors can include one or more logic devices, such as small-scale integrated circuits, programmable logic arrays, programmable logic devices, masked-programmed gate arrays, field programmable gate arrays (FPGAs), application specific integrated circuits (ASICs), and complex programmable logic devices (CPLDs). Logic devices can include, without limitation, arithmetic logic blocks and operators, registers, finite state machines, multiplexers, accumulators, comparators, counters, look-up tables, gates, latches, flip-flops, input and output ports, carry in and carry out ports, and parity generators, and interconnection resources for logic blocks, logic units and logic cells.

The computing device includes memory or storage, which can be accessed by the system bus or in any other manner. Memory can store control logic, instructions, and/or data. Memory can include transitory memory, such as cache memory, random access memory (RAM), static random access memory (SRAM), main memory, dynamic random access memory (DRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), one time programmable non-volatile memory (OTPNVM), hard disk drives, optical storage devices, compact disc drives, flash drives, floppy disk drives, magnetic tape drives, memory chips, and memristor memory cells. Non-transitory memory can be provided on a removable storage device. A computer-readable medium can include any physical medium that is capable of encoding instructions and/or storing data that can be subsequently used by a processor to implement embodiments of the method and system described herein. Physical media can include floppy discs, optical discs, CDs, mini- CDs, DVDs, HD-DVDs, Blu-ray discs, hard drives, tape drives, flash memory, or memory chips. Any other type of tangible, non-transitory storage that can provide instructions and/or data to a processor can be used in these embodiments.

The computing device can include one or more input/output interfaces for connecting input and output devices to various other components of the computing device. Input and output devices can include, without limitation, keyboards, mice, joysticks, microphones, cameras, displays, touchscreens, monitors, scanners, speakers, and printers. Interfaces can include universal serial bus (USB) ports, serial ports, parallel ports, game ports, and the like.

The computing device can access a network over a network connection that provides the computing device with telecommunications capabilities. Network connection enables the computing device to communicate and interact with any combination of remote devices, remote networks, and remote entities via a communications link. The communications link can be any type of communication link, including without limitation a wired or wireless link. For example, the network connection can allow the computing device to communicate with remote devices over a network, which can be a wired and/or a wireless network, and which can include any combination of intranet, local area networks (LANs), enterprise-wide networks, medium area networks, wide area networks (WANs), the Internet, cellular networks, and the like. Control logic and/or data can be transmitted to and from the computing device via the network connection. The network connection can include a modem, a network interface (such as an Ethernet card), a communication port, a PCMCIA slot and card, or the like to enable transmission of and receipt of data via the communications link.

The computing device can include a browser and a display that allow a user to browse and view pages or other content served by a web server over the communications link. A web server, server, and database can be located at the same or at different locations and can be part of the same computing device, different computing devices, or distributed across a network. A data center can be located at a remote location and accessed by the computing device over a network.

The computer system can include architecture distributed over one or more networks, such as, for example, a cloud computing architecture. Cloud computing includes without limitation distributed network architectures for providing, for example, software as a service (SaaS), infrastructure as a service (IaaS), platform as a service (PaaS), network as a service (NaaS), data as a service (DaaS), database as a service (DBaaS), desktop as a service (DaaS), backend as a service (BaaS), test environment as a service (TEaaS), API as a service (APIaaS), and integration platform as a service (IPaaS).

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A system for storing objects, comprising:
an object recognition device;
a computer system in communication with the object recognition device and usable with an automated storage system, the computer system comprising a controller and memory including a database for storing object identification and storage location data, the computer system being operative to execute instructions to:
recognize an object interfacing with the object recognition device,
add a recognized object to a job list, the job list including at least one job having an object identification and a storage location, and
store the job list in the memory in a location accessible to the automated storage system;
wherein the automated storage system comprises a plurality of storage locations, wherein the automated storage system is positionable in an object loading or unloading position at which each object usable with the automated storage system is retrievable or storable, and wherein the automated storage system is operative to:
scan a folder to identify each of the at least one job in the job list;
display each of the at least one identified job;
receive an input for one or more of the at least one identified job to carry out execution thereof;
display an object to be stored or retrieved; and
position the automated storage system in the object loading or unloading position for carrying out the at least one identified job for execution.

2. The system of claim 1, wherein the job list includes a plurality of jobs for multiple objects, each of the multiple objects having an identification and a storage location selected from the plurality of storage locations, and a quantity of the objects to be stored at each location.

3. The system of claim 1, wherein the job list is stored within a job file accessible in the folder by the object recognition device and the automated storage system.

4. The system of claim 1, wherein the computer system is operative to:
receive an input from a user creating a new job;
determine an object type for the recognized object and display to the user an identification of a staging bin for the recognized object type;
repeat the input receiving and the object type determination for multiple objects to be stored; and
create a job file containing the job list.

5. The system of claim 1, wherein the database further includes one or more categories of object types, user-specific data relating to recognized objects, and recognition data for the recognized object, the recognition data including one or more of an image, measurements, a barcode, and an RFID value for the recognized object.

6. The system of claim 1, wherein step (a) further comprises:
placing the object to be recognized on the object recognition device;
determining measurements of the object; and
comparing the measurements of the object to be recognized with stored measurements in the database to find an object type with similar measurements.

7. The system of claim 6, wherein the controller is further operative to:
receive a quantity of the object type to be stored;
update an inventory with the quantity to be stored; and
provide the storage location for the object to be stored.

8. The system of claim 1, wherein the controller is further operative to:
receive an input comprising an identification of a desired object type to be retrieved from storage;
provide an indication of a storage location and current inventory quantities for the desired object type;
receive an input comprising a quantity of the desired object type to be retrieved from storage; and
update an inventory of the desired object type.

9. A method for storing objects, comprising:
recognizing an object with an object recognition device;
adding a recognized object to a job list, the job list including at least one job having an object identification and a location;
storing the job list in a memory in a location accessible to an automated storage system;
scanning a folder to identify each of the at least one job in the job list;
displaying each of the at least one identified job;
receiving an input for one or more of the at least one identified job to carry out execution thereof;
displaying an object to be stored or retrieved; and
position an automated storage system in an object loading or unloading position for carrying out the at least one identified job for execution.

10. The method of claim 9, wherein the job list includes a plurality of jobs for multiple objects, and the automated storage system stores each of the multiple objects in an order different from an order in which the multiple objects are listed in the job list.

11. A system for storing objects, comprising:
an object recognition device;
a computer system in communication with the object recognition device and usable with a storage system, the computer system comprising a controller and memory including a database for storing object identification and storage location data, the computer system being operative to execute instructions to:
recognize an object interfacing with the object recognition device,
add a recognized object to a job list, the job list including at least one job having an object identification and a storage location, and
store the job list in the memory in a location accessible to the storage system;
wherein the storage system comprises a plurality of storage locations, wherein the storage system is positionable in an object loading or unloading position at which each object usable with the storage system is retrievable or storable, and wherein the storage system is operative to:
scan a folder to identify each of the at least one job in the job list,
display each of the at least one identified job,
receive an input for one or more of the at least one identified job to carry out execution thereof,
display an object to be stored or retrieved, and
output a signal indicating a position of the storage system in the object loading or unloading position for carrying out the at least one identified job for execution.

12. A system for storing objects, comprising:
an object recognition device;
a computer system in communication with the object recognition device and a storage system, the computer system comprising a controller and memory including a database for storing object identification and storage location data, the computer system being operative to execute instructions to:
recognize an object interfacing with the object recognition device,
add a recognized object to a job list, the job list including at least one job having an object identification and a storage location, and
store the job list in the memory in a location accessible to the storage system; and
a storage system comprising a plurality of storage locations, wherein the storage system is positionable in an object loading or unloading position at which each object usable with the storage system is retrievable or storable, and wherein the storage system is operative to:
scan a folder to identify each of the at least one job in the job list;
display each of the at least one identified job;
receive an input for one or more of the at least one identified job to carry out execution thereof;
display an object to be stored or retrieved; and
position the storage system in the object loading or unloading position for carrying out the at least one identified job for execution.

13. A system for storing objects, comprising:
an object recognition device; and
a computer system in communication with the object recognition device and usable with a storage system positionable in an object loading or unloading position at which each object usable with the automated storage system is retrievable or storable, the computer system comprising a controller and memory including a database for storing object identification and storage location data, the computer system being operative to execute instructions to:
recognize an object interfacing with the object recognition device,
add a recognized object to a job list, the job list including at least one job having an object identification and a storage location,
store the job list in the memory,
receive, from the storage system, one or more requests each identifying one of the at least one job in the job list,
transmit, to the storage system, each of the at least one job requested,
receive an input for each of the at least one job requested to carry out execution thereof,
display an object to be stored or retrieved, and
output a signal corresponding to a position of the automated storage system in the object loading or unloading position for carrying out the at least one job requested for execution.

\* \* \* \* \*